(12) United States Patent
Olson

(10) Patent No.: US 7,407,498 B2
(45) Date of Patent: Aug. 5, 2008

(54) CONSTRUCTION OF MEDICAL COMPONENTS USING GAS ASSISTED MICROCELLULAR FOAMING

(75) Inventor: Greg Olson, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 169 days.

(21) Appl. No.: 10/653,123

(22) Filed: Sep. 2, 2003

(65) Prior Publication Data

US 2005/0049545 A1    Mar. 3, 2005

(51) Int. Cl.
*A61M 25/16* (2006.01)

(52) U.S. Cl. .................. 604/534; 604/264; 604/523; 604/525; 604/533; 428/317.9; 428/316.6; 428/319.1; 428/319.3; 428/319.7

(58) Field of Classification Search ............. 428/304.4, 428/317.9, 316.6, 319.1, 319.3, 319.7; 604/21, 604/264, 523, 525, 533, 534

See application file for complete search history.

(56) References Cited

U.S. PATENT DOCUMENTS

| | | | |
|---|---|---|---|
| 4,473,665 A | 9/1984 | Martini-Vvedensky et al. | 521/79 |
| 4,539,256 A * | 9/1985 | Shipman | 428/315.5 |
| 4,832,770 A | 5/1989 | Nojiri et al. | 156/78 |
| 4,940,736 A | 7/1990 | Alteepping et al. | 521/98 |
| 5,081,161 A * | 1/1992 | Ostapchenko | 521/61 |
| 5,116,881 A | 5/1992 | Park et al. | 521/143 |
| 5,158,986 A | 10/1992 | Cha et al. | 521/82 |
| 5,180,751 A | 1/1993 | Park et al. | 521/51 |
| 5,358,675 A | 10/1994 | Campbell et al. | 264/50 |
| 5,369,135 A | 11/1994 | Campbell et al. | 521/134 |
| 5,462,974 A | 10/1995 | Lee | 521/79 |
| 5,525,697 A | 6/1996 | De Vos et al. | 528/59 |
| 5,614,136 A | 3/1997 | Pepin et al. | 264/40.3 |
| 5,667,728 A | 9/1997 | Lee | 252/350 |
| 5,679,718 A | 10/1997 | Suh et al. | 521/53 |
| 5,801,208 A | 9/1998 | Lee | 521/98 |
| 5,851,464 A | 12/1998 | Davila et al. | 264/103 |
| 5,854,295 A | 12/1998 | Suh et al. | 521/82 |
| 5,866,053 A | 2/1999 | Park et al. | 264/50 |

(Continued)

FOREIGN PATENT DOCUMENTS

EP    0 616 817 A1    9/1994

(Continued)

OTHER PUBLICATIONS

Weng, Dexi; Andries, John; Morin, Phil; Saunders, Keith; Politis, John, "Fundamentals and Material Development for Thermoplastic Elastomer (TOE) Overmolding," *Journal of Injection Molding Technology* (2000), 4(1), 22-28.

(Continued)

*Primary Examiner*—Hai Vo
(74) *Attorney, Agent, or Firm*—Vidas, Arrett & Steinkraus

(57) ABSTRACT

A method of forming a medical device or components thereof, including the steps of providing a first component of said medical device which is formed a first material and providing a second polymeric material into a mold cavity to overmold a second component of the medical device over the first component, and wherein the second polymeric material is further injected with a blowing agent to form a foam, and to components and to the medical devices made therefrom.

10 Claims, 3 Drawing Sheets

U.S. PATENT DOCUMENTS

| | | | |
|---|---|---|---|
| 5,969,020 A | 10/1999 | Shalaby et al. | 524/167 |
| 6,169,122 B1 | 1/2001 | Blizard et al. | 521/79 |
| 6,231,942 B1 | 5/2001 | Blizard et al. | 428/36.5 |
| 6,235,380 B1 | 5/2001 | Tupil et al. | 428/314.4 |
| 6,273,404 B1 * | 8/2001 | Holman et al. | 264/276 |
| 6,284,810 B1 | 9/2001 | Burnham et al. | 521/79 |
| 6,294,115 B1 | 9/2001 | Blizard et al. | 264/45.9 |
| 6,322,347 B1 | 11/2001 | Xu | 425/376.1 |
| 6,368,315 B1 * | 4/2002 | Gillis et al. | 604/523 |
| 6,376,059 B1 | 4/2002 | Anderson et al. | 428/314.8 |
| 6,519,835 B1 | 2/2003 | Von Arx et al. | 29/611 |
| 6,527,703 B2 * | 3/2003 | Simmet | 600/33 |
| 6,565,763 B1 | 5/2003 | Asakawa et al. | 216/56 |
| 6,575,959 B1 | 6/2003 | Sarge et al. | 604/533 |
| 6,579,910 B2 | 6/2003 | Xu | 521/79 |
| 6,583,190 B2 | 6/2003 | Lee et al. | 521/97 |
| 6,593,384 B2 | 7/2003 | Anderson et al. | 521/97 |
| 6,602,063 B1 | 8/2003 | Cardona | 425/4 |
| 6,602,064 B1 | 8/2003 | Chen et al. | 425/4 |
| 6,613,811 B1 | 9/2003 | Pallaver et al. | 521/81 |
| 6,616,434 B1 | 9/2003 | Burnham et al. | 425/4 |
| 6,630,086 B1 * | 10/2003 | Goral et al. | 264/40.4 |
| 6,764,461 B2 * | 7/2004 | Mickley et al. | 604/15 |
| 2002/0188216 A1 * | 12/2002 | Kayyali et al. | |
| 2003/0004493 A1 | 1/2003 | Casey et al. | 604/525 |
| 2004/0088038 A1 * | 5/2004 | Dehnad et al. | |
| 2004/0122464 A1 * | 6/2004 | Wang et al. | |
| 2005/0148720 A1 * | 7/2005 | Li et al. | 524/474 |

FOREIGN PATENT DOCUMENTS

WO     WO 9505083 A1 *   2/1995

OTHER PUBLICATIONS

Haberstroh, E.; Ronnewinkel, C., "LSR Thermoplastic Combination Parts in Two-Component Injection Molding," *Journal of Polymer Engineering* (2001), 21 (2-3), 303-318.

Love, J.C.; Goodship, V., "Multi-Material Injection Molding," *Rapra Review Reports* (2002), 13 (1) 1-32.

* cited by examiner

CONSTRUCTION OF MEDICAL COMPONENTS USING GAS ASSISTED MICROCELLULAR FOAMING

FIELD OF THE INVENTION

The present invention relates to the construction of components for medical devices using gas assisted microcellular foaming.

BACKGROUND OF THE INVENTION

The use of catheters in guiding, diagnostic, therapeutic, and other interventional procedures is known. One commonly used type of catheter is the intravascular catheter employed for the treatment of cardiovascular disease. An even more specific type of catheter is that which is employed in percutaneous translumenal coronary angioplasty (PTCA). PTCA procedures have gained wide acceptance in recent years as efficient and effective methods for treating types of vascular disease and are commonly used for opening stenoses in the coronary arteries and are used for treating stenoses in other vascular regions as well.

PTCA is well known in the art and typically involves the use of a guide catheter, a guide wire and a balloon catheter, possibly in combination with other intravascular devices. A typical balloon catheter has an elongate shaft with a balloon attached proximate its distal end and an inflation manifold attached proximate the proximal end. In use, the balloon catheter is advanced through a lumen in the guide catheter over the guide wire such that the balloon is positioned adjacent a restriction in a diseased vessel. The balloon is then inflated and the restriction in the vessel is opened.

Current PTCA catheters also often have a short strain relief surrounding a hypotube segment or other polymeric shafts having one or more lumens that form the proximal shaft of the catheter. Hypotubes, or thin-walled polymeric tubing used for catheter shafts, can kink if bent too sharply. Strain reliefs are commonly formed of a polymeric material extending distally from a manifold affixed to the proximal end of a catheter shaft. The current designs can inhibit kinking where the hypotube or polymeric tube exits the manifold within the strain relief.

Guiding catheters are generally comprised of a shaft which is hollow, defining an inner lumen. The shaft is generally comprised of two tubes congruent to each other with a support member therebetween. A hub is connected to the proximal end of the shaft to provide a means for connecting another device such as a syringe to inject fluids, or for providing a means to direct the device in order to place it within the vessel. A tip of a desired shape is provided at the distal end of the shaft.

Furthermore, due to the fact that catheters are maneuvered through very small body lumen, they have specific flexibility requirements that vary with the location along the catheter length. Less flexibility may be required in the catheter proximal portion, where the catheter may lie within a large inside diameter, straight vessel portion. Greater flexibility is often a design goal in the catheter distal portion, where traversing small inside diameter, tortuous vessels may be required. In the catheter mid-region, a gradually, distally increasing flexibility is desirable rather than an abrupt change from low to high flexibility.

Thus, catheter construction often involves various sections which are formed from different polymeric materials depending on the physical requirements of the particular section. For example, catheter construction may involve the formation of an inner shaft with a relatively low melting temperature polymeric material and formation of the manifold with a relatively higher melting temperature polymeric material.

However, molding two such different polymeric materials together can be difficult due to the differences in melting temperature of the materials employed in making the various catheter components. Relatively lower melting temperature polymeric materials may be employed in formation of an inner shaft, for example, while a manifold may be formed from a relatively higher melting temperature polymeric material which, if molded over the inner shaft, can result in deformation of the inner shaft at the temperatures required for processing the relatively higher melting temperature polymeric material to form the manifold. This may lead to defective parts. Consequently, the manifold and the inner shaft are typically molded separately and then later secured together using standard techniques such as adhesive bonding or through welding if possible. Obviously, this requires more steps and less efficiency in the manufacturing process. This is only one example of how various components of a catheter device may be manufactured and assembled.

Thus, there remains a need in the art for a more efficient way to manufacture such catheter devices, as well as improved catheter devices themselves which meet the flexibility and other performance characteristics required.

SUMMARY OF THE INVENTION

The present invention relates to a novel method of constructing medical devices and components thereof, and to the devices made thereby, wherein at least one component is formed from a polymeric foam, in particular a microcellular polymeric foam.

In one aspect, the present invention relates to a medical device formed according to the method described herein, wherein components formed from relatively higher melting temperature polymeric materials may be directly overmolded onto another component. The latter component may be formed from polymeric materials as well, but it may also be formed from other materials such as metals and alloys thereof including stainless steel, for example, as in the formation of a stainless steel hypotube, or ceramics, and so forth.

The present invention is particularly useful, however, wherein a first component is formed from a first polymeric material and a second component which is direct contact with the first component is formed from a second polymeric material which has a higher melting temperature than the first polymeric material.

The invention allows simultaneous formation of the first and second components in first and second mold cavities, i.e. overmolding of the second component over the first component, which otherwise cannot be formed at the same time due to deformation of the first component caused by higher processing temperatures required to form the second polymeric component.

However, while the present invention may be used to simultaneously form parts that would not otherwise be formed at the same time, this is not to say that it cannot be used in a serial process in which a first part is formed and placed into the second tool and then the second part is overmolded onto the first.

Thus, in one embodiment, the method according to the present invention includes the steps forming a first component from a first polymeric material in a mold and simultaneously overmolding a second component formed from a second polymeric material over the first component. The second component is formed from of a foamed polymeric material. Polymeric foams include a plurality of voids, also called cells, in a polymer matrix.

Desirably, the foam is a microcellular foam. Microcellular foams have smaller cell sizes and higher cell densities than conventional polymeric foams. Several patents and patent publications describe aspects of microcellular materials and microcellular processes. For example, U.S. Pat. Nos. 4,473,665, 5,158,986, 5,866,053, 6,593,384, and so forth, describe such foams and are each herein incorporated by reference in their entirety.

The method according to the invention can be used advantageously when the first polymeric material has a lower melting temperature than said second polymeric material, although the method is not limited as such. By adding an inert gas or other blowing agent to the higher melting component, the viscosity is effectively decreased, and the processing temperature can be lowered, thus, a higher melting temperature material may be overmolded onto a component formed from a lower melting temperature material without damage and deformation to the component formed form the lower melting temperature material as a result of processing temperatures which are too high. Of course, the method according to the invention is not limited to such cases.

Thus, foaming of the second higher melting polymeric material allows the second component to be formed directly over the first component even though it is formed from a material with a higher melting temperature.

The method includes the addition of a chemical and/or physical blowing agent by mixing or injection into a molten polymeric stream of an blowing agent during the molding process which sufficiently lowers the viscosity and consequently the required processing or molding temperature of the higher melting polymeric material thereby allowing overmolding of one higher melting polymeric material over another, a process that may otherwise not be possible. Thus, the method according to the present invention allows components formed from polymeric materials having different melting temperatures to be molded together, even when the melting temperatures are quite different. This process minimizes the damage that may occur to the component formed from the lower melting material.

Different components of medical devices are currently formed from materials having different melting temperatures but in order to secure such components together has heretofore required either an additional adhesive, or has required welding of the materials. If materials of different compatibilities are welded together, an additional tie layer may also be required. Thus, the present invention simplifies the process by which the medical device is manufactured.

The present invention finds particular utility in the construction of intravascular medical devices, and more specifically to the construction of any type of catheters including guide, diagnostic, and therapeutic catheters for use in medical procedures such as for interventional radiology, angiography, angioplasty, i.e. balloon catheters, cardiac ablation catheters, catheters used in the urinary tract, reproductive system, and so forth.

A variety of catheter types and uses therefore are described, for example, in U.S. Pat. No. 6,575,959 which is incorporated by reference herein in its entirety.

More specifically, the present invention allows for overmolding of a manifold/strain relief, tip, marker band, gripping and constraining structure, and so forth, to a catheter shaft, for example.

The present invention allows for reduction of material for a given volume, as well as lower processing temperatures due to lower viscosities obtained with a foamed polymeric material.

DETAILED DESCRIPTIONS OF THE INVENTION

Figure 1:
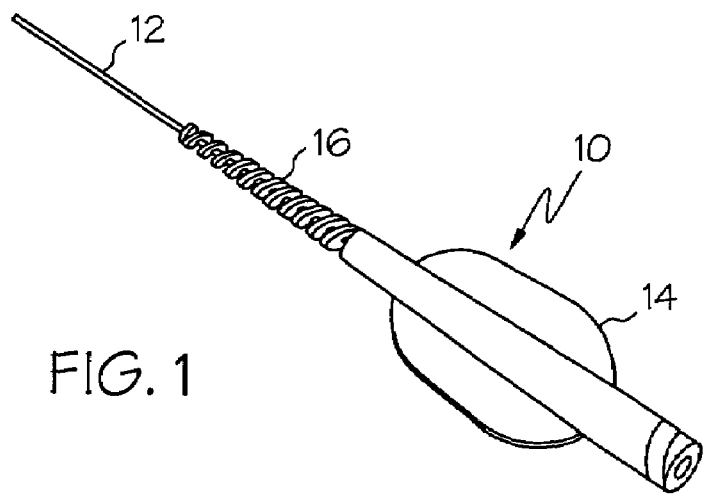
FIG. 1 is a side view of a catheter having a manifold/strain relief, overmolded onto an outer.

While this invention may be embodied in many different forms, there are described in detail herein specific embodiments of the invention. This description is an exemplification of the principles of the invention and is not intended to limit the invention to the particular embodiments illustrated.

The present invention relates generally to the use of foaming techniques in the formation of medical devices and components thereof which are formed from polymeric materials. Of course, the polymeric components may be employed in combination with other non-polymeric components in the formation of medical devices such components formed from metals and metal alloys, ceramic, and so forth. Polymeric foams include a plurality of voids, also called cells, in a polymer matrix. Suitably, the resultant foam is a microcellular foam. Microcellular foams have smaller cell sizes and higher cell densities than conventional polymeric foams. Typically, microcellular foams are defined as having average cell sizes of less than 100 microns and a cell density of greater than $10^6$ cells/cm$^3$ of solid plastic.

The foam may be formed using any technique known in the art. Formation of polymeric foams and microcellular foams is discussed, for example, in U.S. Pat. Nos. 4,473,665, 4,832, 770, 4,940,736, 5,116,881, 5,158,986, 5,180,751, 5,358,675, 5,369,135, 5,679,718, 5,854,295, 5,866,053, 6,169,122, 6,231,942, 6,235,380, 6,284,810, 6,294,115, 6,322,347, 6,376,059, each of which is incorporated by reference herein in their entirety.

In forming a polymeric foam material according to the invention, nucleating agents may optionally be incorporated into the polymer melt to promote cell nucleation. A nucleating agent is often a particulate of small particle size that may be added to and dispersed within the polymer melt, and is able to promote formation of nucleation sites from a single-phase, homogeneous solution. Such agents can be a variety of compositions. One class of nucleating agents is the solid inorganic particles. Specific examples include, but are not limited to, talc and calcium carbonate. Nucleating agents are typically incorporated into the polymer melt to promote cell nucleation. The dispersion of nucleating agents within the polymer mixture promotes formation of a uniform cell structure. Such nucleating agents are known to those of ordinary skill in the art.

Nucleating agents are typically added into the polymer melt during processing. Typically, these nucleating agents are incorporated into the polymer melt at levels of less than 1% by weight up to about 10% by weight of the polymeric melt to lower the energy required for cell nucleation. Nucleation is discussed in U.S. Pat. No. 6,294,115 and 6,593,384, each of which is incorporated by reference herein in its entirety.

The foam may be produced using any means known in the art, typically through the introduction into the polymeric melt of chemical and/or physical blowing agents. A chemical blowing agent is typically mixed with the polymer. The chemical blowing agent undergoes a chemical reaction in the polymeric material, typically under conditions in which the polymer is molten, causing formation of a gas. Chemical blowing agents generally are low molecular weight organic compounds that decompose at a particular temperature and release a gas such as nitrogen, carbon dioxide, or carbon monoxide.

According to another technique a physical blowing agent, i.e., a fluid that is a gas under ambient conditions, is injected into a molten polymeric stream to form a mixture. The mixture is subjected to a pressure drop, causing the blowing agent to expand and form bubbles (cells) in the polymer. Exposure to atmospheric conditions causes the blowing agent to gasify, thereby forming cells in the polymer. Both open and closed cell foams may be produced depending on the conditions under which foaming occurs. As an alternative to a physical blowing agent, a chemical blowing agent can be used which undergoes chemical decomposition in the polymer material causing formation of a gas, as well as any combinations thereof may be employed.

Any of a wide variety of chemical and physical blowing agents known to those of ordinary skill in the art may be employed herein. Some conventional blowing agents include, but are not limited to, volatile organic compounds (VOCs) which include the light, aliphatic hydrocarbons such as the $C_3$ to $C_5$ hydrocarbons (HCs) such as propane, n-butane, isobutane, butylene, isobutene, pentane, isopentane, cyclopentane, neopentane, hexane, and so forth, and other HCs including hexane and cyclohexane; methylene chloride; chlorofluorocarbons (CFCs) such as trichlorofluoromethane (CFC-11); hydrochlorofluorocarbons (HCFCs); dialkyl ethers; alkyl alkanoates; aliphatic and cycloaliphatic hydrofluorocarbons; hydrochlorocarbons; fluorine-containing ethers; and so forth.

Physical blowing agents are typically gaseous in nature. Any gas can be used, including nitrogen, carbon dioxide, helium, argon, $NO_x$, xenon, krypton, and so forth. Nitrogen and carbon dioxide, in particular, have the advantage of being inexpensive, readily available, are not flammable, and are not considered to be harmful to the earth's ozone layer.

Blowing agents provided in a supercritical fluid state in the extruder may also be employed including supercritical carbon dioxide and supercritical nitrogen.

Blowing agents may be added in amounts of less than about 1wt-% and up to about 15wt-% based on the weight of the polymeric material and the blowing agent. Blowing agents are described for use in amounts of less than 1% in U.S. Pat. No. 6,593,384 which is incorporated by reference herein in its entirety.

Blowing agents may also be employed in mixtures, including mixtures of chemical and/or physical blowing agents.

The above blowing agents are intended for illustrative purposes only, and are not intended to limit the scope of the present invention. Blowing agents are known in the art and are discussed in, for example, U.S. Pat. Nos. 5,525,697, 5,369,135, 5,462,974, 5,667,728, 5,801,208, 5,866,053, 6,583,190, 6,593,384, each of which is incorporated by reference herein in its entirety.

The present invention may be employed in the formation of all types of medical devices and components thereof. Some examples include, catheter assemblies and the components thereof including, but not limited to, catheter shafts and tips, manifolds, strain reliefs, constraining structures, gripping structures, markers, and so forth. One of ordinary skill in the art would know that the present invention may be employed for a variety of such components and the invention is not limited to those listed herein. Some more specific embodiments are discussed hereinafter.

Both elastomeric and non-elastomeric polymers may be employed in the formation of the medical device components formed herein. Polymeric materials suitable for use herein include, but are not limited to, polycarbonates; polyamides including linear polyamides and nylon 6/6, nylon 12, nylon 11, nylon 6, and so forth; polyolefins including polyethylene and polypropylene; polystyrenes, polyurethanes; polyesters including linear polyesters; silicones; copolymers of such materials including polyether-block-amides, polybutylene terephthalate, polyethylene terephthalate; cyclic olefin copolymers; styrenic block copolymers; any other copolymers thereof; and so forth. As used herein, the term copolymer shall be used to refer to any polymer formed from more than one monomer.

More specific examples of polymeric materials suitable for use herein include, but are not limited to, polyesters and copolymers thereof such as those sold including polyalkylene terephthalates such as polyethylene terephthalate (PET) and polybutylene terephthalate (PBT) available under the tradename of EKTAR® available from Eastman Chemical Co. in Kingsport, Tenn., polycyclohexylene terephthalate (PCT); poly(trimethylene terephthalate) (PTT), PCTG and poly(cyclohexanedimethanol-co-ethylene terephthalate) (PETG) copolyesters available under the tradename of EASTAR® available from Eastman Chemical Co., PCTA available under the tradename of DURASTAR® available from Eastman Chemical Co., poly(ethylene naphthalate) (PEN} polyester available from DuPont in Wilmington, Del. under the tradename of TEONEX®; and so forth; polyester elastomers (PEELs); polyamides such as amorphous nylon and nylon 12 such as those available from Elf Atochem under the tradename of CRISTAMID® and copolymers thereof such as GRILAMID® TR-55-LX nylon 12 polyether-block-amide available from EMS-American Grilon in Sumter, SC; polyetherimides available from GE Plastics under the tradename of ULTEM®; polystyrene and expandable polystyrene (EPS); acrylonitrile-butadiene-styrene (ABS); styrene-acrylonitrile (SANs); polyphenylene sulfide (PPS); polyphenylene oxides (PPO); interpolymers of PPO and EPS; polyetherketones (PEEK); polyolefins such as polyethylenes and polypropylenes including low, medium and high densities such as HDPE available under the tradename of ALATHON® from; amorphous polyolefins; polyether-block-amides such as those sold under the tradename of PEBAX® including 6333 SA01 available from Elf Atochem; to mention only a few as well as any copolymers thereof. The above list is intended for illustrative purposes only, and is not intended to limit the scope of the present invention. One of ordinary skill in the art has knowledge of such polymeric materials.

As used herein, the term "copolymer" shall be used to encompass any polymer formed from more than one monomer.

Using the method according to the invention allows for overmolding of one material onto another. For examples, manifolds, tips, marker bands, tips, gripping structures, constraining structures, and so forth, may be overmolded onto a catheter shaft.

While any of the materials discussed above may be employed in the material which is to be overmolded, some specific examples of materials which may be employed in overmolding of a catheter component include, but are not limited to, polystyrene; ABS; SANs; polyurethanes (PURs); block copolymers including the styrenic block copolymers and polyether-block-amides such as those available under the tradename of PEBAX® including 70D, 6333 and 7233; polyesters and copolyesters; polyolefins such as the polyethylenes including low, medium, high and ultra high density polyethylenes and polypropylenes and cyclic olefin copolymers (COC); polyamides including the nylons such as nylon 12 and nylon 12 polyether block amide available under the tradename of GRILAMID®; copolymers of olefinic materials such as high density ethylene-hexene copolymers; liquid silicone rubber (LSR); and so forth; as well as any copolymers thereof. These materials are intended for illustrative purposes only, and are not intended to limit the scope of the present invention. Such polymeric materials suitable for use herein are known to those of ordinary skill in the art.

As noted above, materials described for tubing, for example, may also be employed for over-molding and visa versa.

Of course, blends of the polymeric materials may also be employed herein, as well as other compounding materials known to those of ordinary skill in the art including for example, but not limited to, fluorescing agents, antioxidants, plasticizers, coupling agents, waxes, materials that change conductivity, and other ingredients known in the art may be employed herein.

The present invention may be employed in the formation of medical devices and components thereof including catheter assemblies and components thereof such as, for example, catheter shafts, tips, manifolds, hubs, strain reliefs, constraining structures, gripping structures, markers, and so forth.

Some specific embodiments for which the present invention may be employed are discussed herein as follows. Turning now to the figures, FIG. 1 illustrates generally at 10, a catheter formed according to the present invention with a manifold/strain relief 14, 16 overmolded onto an outer catheter shaft. In this embodiment, the outer shaft may be formed from any suitable polymeric material as discussed above. Specific examples include, polyamides and copolymers thereof such as nylon 12, polyether block amide, or nylon 12 polyether block amide such as those available under the tradename of GRILAMID® from EMS-GRILTECH, such as GRILAMID® TR-55-LX. The manifold/strain relief 14,16 may be formed from a rigid thermoplastic material such as a rigid polyurethane, for example. One example of such a material is that available from under the tradename of ISO-PLAST® SUCH AS ISOPLAST® 2530 Polyurethane.

Manifold/strain relief 14,16 are overmolded on to the outer 12. The manifold/strain relief 14, 16 may be injection molded over the outer 12 even though the melting temperature of the polymeric material employed in the manifold/strain relief 14, 16 is higher. This is accomplished by employing a foaming technique whereby inert gas is injected into the nylon 12 material during the molding process. As defined herein, a foamed polymeric material is one having a plurality of cells or voids resulting from use of a blowing agent which is injected, or otherwise forced into the polymeric material. Such a technique results in a lower viscosity allowing for a lower processing temperature.

Manifolds may be formed from any of a variety of suitable polymeric materials including those described above. In some embodiments, the manifold may be formed from polyamides and copolymers thereof, including, for example, GRILAMID® TR-55-LX, a nylon 12 polyether-block-amide copolymer, such as those sold under the tradename of PEBAX® including 70D, 6333 and 7233 polyether-block-amide copolymers available from Elf Atochem North America in Philadelphia, Pa.; polyurethanes such as ISO-PLAST® 2530 amorphous polyurethane available from Dow Chemical Co. in Midland, Mich. and TECOPLAST® TP-470 series of aromatic polyether based thermoplastic polyurethanes available from Thermedics Polymer Products a division of VIASYS Healthcare in Wilmington, Mass.; thermoplastic polyester elastomers such as those available from DSM Engineering Plastics in Evansville, Ind. under the tradename of ARNITEL® which are polyether-ester elastomers; polyolefins and olefinic copolymers including high density polyethylenes available from Dow Chemical Co. in Midland, Mich. such as Dow 4903 and REXENE® 7076 available from Rexene Corp. in Dallas, Tex., those available under the tradename of ALATHON® such as ALATHON® M6020 available from Equistar Chemical Co. in Houston, Tex., and cyclic olefin copolymers such as TOPAS® 8007S-04 copolymers of ethylene and norbornene available from Ticona in Summit, N.J.; and polystyrene available from Huntsman Corp. in Salt Lake City, Utah such as those designated as 266, 331 and 1016; silicones such as Med-4905 liquid silicone elastomer available from NuSil Technology in Carpinteria, Calif. ;styrenic block copolymers such as those available under the tradename of KRATON® such as KRATON® 50A available from the Kraton Polymers Group in Belpre, Ohio; and so forth.

Strain reliefs may also be formed from a variety of materials. Some specific examples of suitable materials include, but are not limited to, polyolefins and copolymers thereof such as low, medium, high and ultra high density polyethylene (PE) such as DOW® LDPE 9591 low density polyethylene and high density ethylene-hexene copolymers such as those available from Qatar Chemical Co. Ltd. in Doha-Qatar under the tradename of MARLEX® such as HHM 4903; KRATON® 50A black, styrenic copolymers such as styrene-acrylonitrile copolymers (SAN); thermoplastic polyester elastomers such as HYTREL® G-3548W; Dow 4903; and so forth.

Catheter tips may also be formed from any suitable polymeric material including those listed and described above. One example of a class of suitable polymers are thermoplastic elastomers including thermoplastic polyester elastomers such as those sold under the tradename of HYTREL(D available from DuPont in Wilmington, Del. including HYTREL® G-3548W, an elastomeric copolyester.

Figure 2:
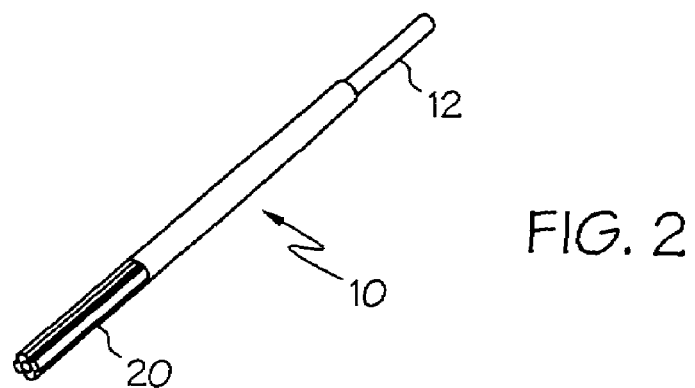
FIG. 2 is a partial view of a catheter device illustrating a tip overmolded onto a catheter shaft.
Figure 3:
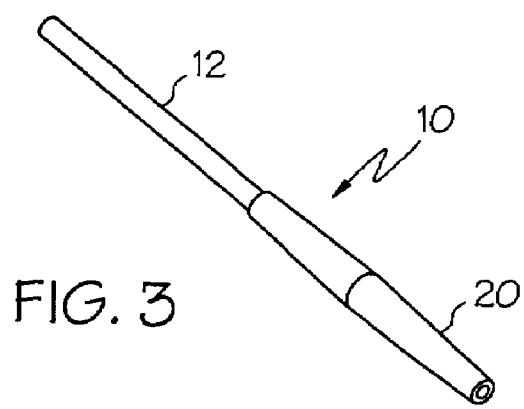
FIG. 3 is a partial view of a catheter device illustrating an alternative tip design wherein the tip is overmolded onto a catheter shaft.

FIGS. 2 and 3 show a partial view of a catheter device 10 showing tips 20 overmolded onto a catheter shaft.

While the present invention is advantageously employed wherein the components which are fitted together are polymeric, the present invention also has utility wherein one component is not polymeric. Examples of non-polymeric materials employed in the formation of medical devices include, but are not limited to metals and metal alloys including stainless steel, alloys formed with chromium, cobalt, nickel, titanium, including, for example, nickel-titanium alloys such as nitinol, noble metals, and so forth, as well as ceramics. This list is intended for illustrative purposes only, and is not intended to limit the scope of the present invention.

Figure 4:
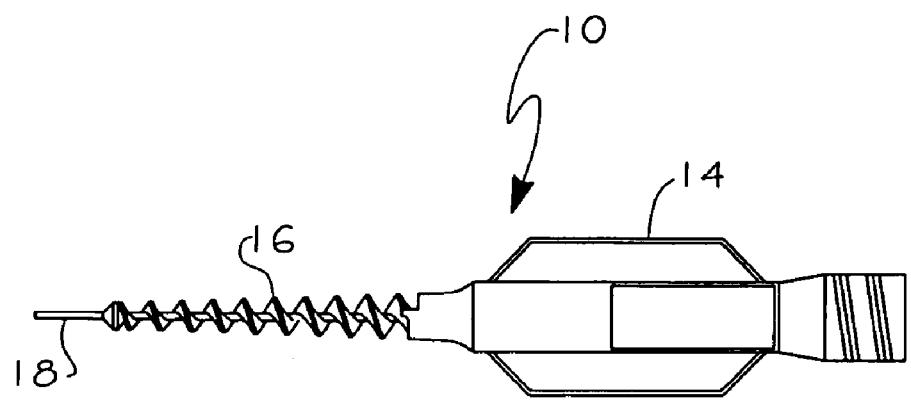
FIG. 4 is a side view of another embodiment of a catheter device according to the present invention with a manifold/strain relief overmolded onto a hypotube.

FIG. 4 is an example of an alternative embodiment of a catheter device 10 in which the manifold/strain relief 14,16 are formed of a polymeric material such as a polycarbonate, which is overmolded onto a metallic hypotube 18 such as one formed from stainless steel, for example. The polycarbonate is injected with an inert gas to form a foam material. Hypotube 18, may also be formed from polymeric materials as well.

Figure 5:
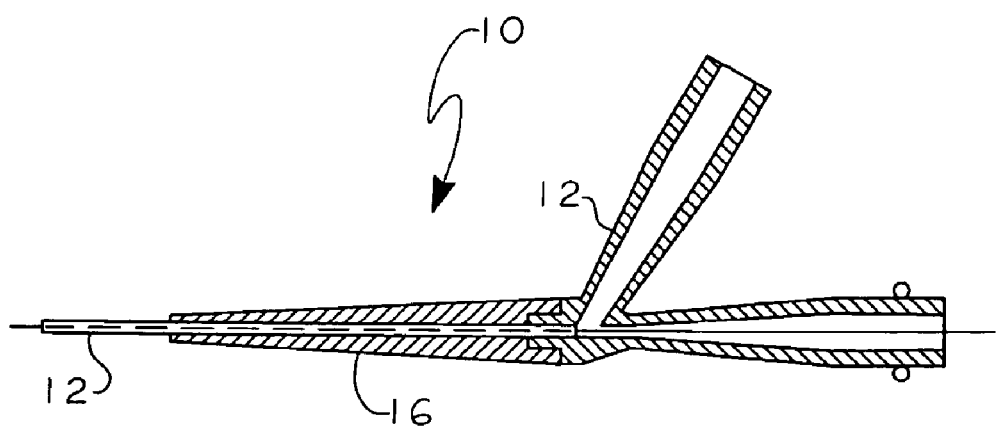
FIG. 5 is side view another embodiment of a catheter device having a manifold/strain relief overmolded onto a catheter shaft.

FIG. 5 illustrates yet another alternative embodiment of a catheter device 10 in which the manifold 14 is formed from a different polymeric material than the strain relief 16, and the catheter shaft 12 is formed from a third polymeric material. Thus, three mold cavities may be employed and inert gas may be injected into both the mold cavity for the manifold 14 and/or the mold cavity for the strain relief 16. In one embodiment, catheter shaft 12 is formed from a polyolefin such as polyethylene, or copolymers thereof. The manifold 14 may be formed from a second polymeric material, for example, another polyolefin such as polypropylene, styrene, copolymers thereof, or mixtures thereof. Strain relief 16 may be formed from yet a third polymeric material such as silicon, for example.

Figure 6:
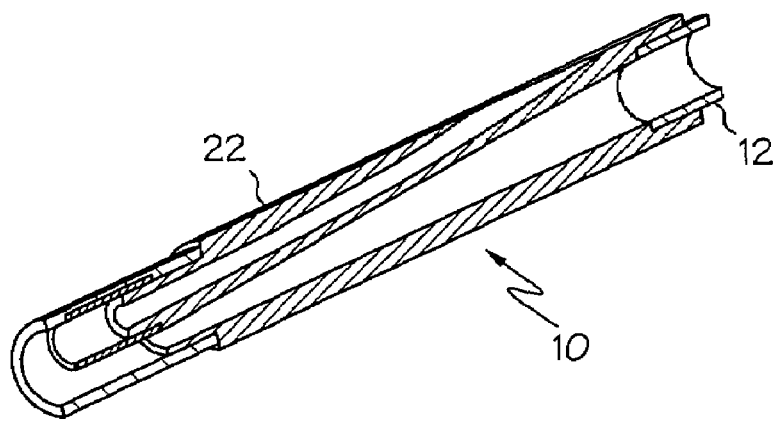
FIG. 6 is a partial fragmented cross-sectional side view of a single operator exchange catheter device.
Figure 7:
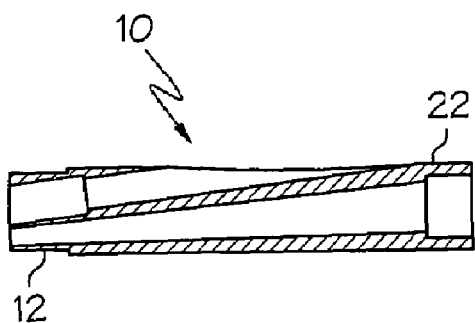
FIG. 7 is a partial non-fragmented cross-sectional side view of the device of FIG. 6.
Figure 8:
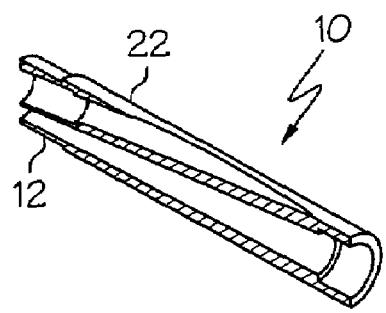
FIG. 8 is an alternative partial fragmented cross-sectional side view of the device of FIGS. 6 and 7.
Figure 9:
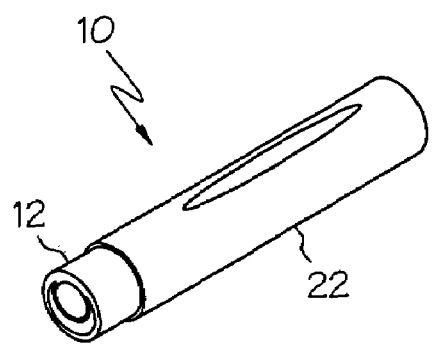
FIG. 9 is a partial non-fragmented side view of the same device as shown in FIGS. 6-8.
Figure 10:
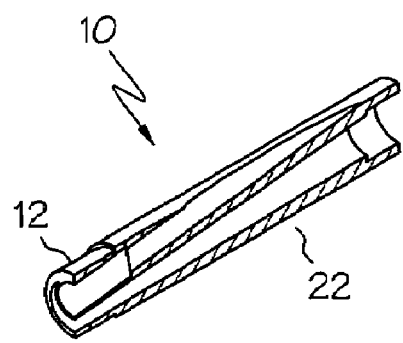
FIG. 10 is another alternative partial fragmented cross-sectional side view of the device of FIGS. 6-9.

FIG. 6 is a fragmented cross-sectional side view of a single operator catheter exchange device 10 having a port 22 such as a guide wire port, which has been overmolded onto catheter shaft 12. FIGS. 7-10 are alternative views of the same catheter device as shown in FIG. 6 wherein FIG. 7 is a cross-sectional longitudinal side view, FIG. 8 is an alternative fragmented cross-sectional side view, FIG. 9 is a side view of the device which has not been fragmented or cut, and FIG. 10 is another alternative fragmented cross-sectional side view of the device.

The components may be formed using any conventional molding techniques known in the art. Typical polymer processing techniques include extrusion, injection molding and blow molding, for example.

The process according to the invention is advantageously used wherein one component of a medical device is formed from a polymeric material which has a higher melting point than the polymeric material from which another component is formed and to which the first component is attached.

As noted above, the present invention is very advantageous where it is desirable to manufacture one component of a medical device from a higher melting polymeric material, and allowing structural integrity to be maintained. Typically, if adjacent components in such a device are manufactured from relatively higher melting temperature polymeric materials, additional assembly is required because the components are not made simultaneously. Thus, in a traditional process, each component is manufactured separately, and then assembled through the use of an additional adhesive, or by welding. This is due to deformation of the component made with the lower melting temperature polymeric material. Welding can be sometimes accomplished without using a tie layer. However, if the components are made from materials which are not compatible, then an additional tie layer may also be required. In either case, additional processing steps are required, thus decreasing the efficiency in the manufacturing process.

The material performance of the adhesive or tie layer can have a negative impact on the structural integrity of the medical device. Furthermore, the addition of a second layer such as an adhesive or tie layer, also may decrease the structural integrity because of the distance increase between the two components of the device. The second layer can also add dimension to the medical device which can be detrimental when manufacturing very small devices such as balloon catheters, where the need is to design smaller and smaller design elements. The method as described herein thus eliminates many of the disadvantages which may be experienced using traditional assembly methods.

Injection of the inert gas blowing agent used during foaming, lowers the viscosity and the temperature required to process the material, consequently allowing manufacture of two adjacent components formed from materials having different melting temperatures. Using the method according to the present invention, allows for overmolding of one component formed from a higher melting polymeric material, directly over a second component formed from a polymeric material which has a lower melting temperature in relation to the polymer from which the first component is formed.

Reducing the viscosity of the material also allows it to flow better facilitating the flow of such material into smaller spaces. This allows the manufacture of smaller parts from more viscous, higher melting temperature materials. Higher melting, higher viscosity materials, often have higher structural integrity, but cannot be used to manufacture small medical device components. Thus, this is also an advantage. Components, or design features, which are less than 0.001" can be made using the foaming technique according to the present invention. Using standard injection molding techniques, it is common to manufacture components having dimensions of about 0.005", but not smaller, with most materials that have wide processing windows or a broad range of conditions under which they can be processed, i.e. the normal limit, down to 0.0015" for those materials which have limited processing windows or limited conditions under which they can be processed.

An additional benefit is that foaming results in less polymeric material being used, thus decreasing costs of manufacturing as well.

The present invention can be advantageously employed to manufacture medical device parts including, but not limited to, tubing of single or multiple lumens used in various catheter devices, catheter manifolds (hubs), catheter tips, midshaft joints, wire exchange ports, marker bands, gripping structures, constraining structures, and so forth.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A catheter comprising a catheter shaft assembly having a proximal end and a distal end, a manifold connected to said catheter shaft assembly at said proximal end, and a tip connected to said catheter shaft assembly at said distal end, said manifold formed from a first polymer composition in microcellular foam form.

2. The catheter of claim 1 wherein said polymeric composition comprises at least one member selected from the group consisting of polyolefins, polyamides, polycarbonates, polyurethanes, polyesters, polyphenylene sulfides, polyphenylene oxides, polyethers, polyirnides, styrenic polymers, silicones, copolymers thereof and mixtures thereof.

3. The catheter of claim 1 wherein said microcellular foam composition comprises a nucleating agent in an amount of about 2.5 to about 7 percent by weight of the polymer material.

4. The catheter of claim 1 wherein said catheter shaft assembly comprises at least one shaft having a proximal end and a distal end, said manifold connected to said proximal end of said at least one shaft of said catheter shaft assembly, said shaft is polymeric or metallic.

5. The catheter assembly of claim 1 wherein said microcellular foam is an essentially closed cell microcellular foam.

6. The catheter of claim 1 wherein said first polymer composition comprises a nucleating agent in an amount of about 1 to about 10 percent by weight of the polymer composition.

7. The catheter of claim 1 wherein said tip is formed from a second polymer composition, said second polymer composition is the same as or different than said first polymer composition, and said second polymer composition is in microcellular foam form.

8. The catheter of claim 1 wherein said manifold further comprising a strain relief, said strain relief formed from a third microcellular foam polymer composition which is the same as or different than said first microcellular foam polymer composition.

9. The catheter of claim 1 wherein said manifold further comprises a gripping structure, said gripping structure formed from a fourth polymer composition which is the same as or different than said first polymer composition, said fourth polymer composition is in a microcellular foam form.

10. A catheter comprising a catheter shaft assembly having a proximal end and a distal end, said catheter shaft assembly comprising at least one catheter shaft, a manifold connected to said catheter shaft assembly at said proximal end, and a tip connected to said catheter shaft assembly at said distal end, said manifold formed from a first polymer composition, said shaft formed from a second polymer composition which is different than said first polymer composition, and said tip formed from a third polymer composition which is different than said first polymer composition and different than said second polymer composition, and at least one of said first polymer composition or said third polymer composition are in microcellular foam form.

* * * * *